(12) United States Patent
Nag et al.

(10) Patent No.: US 6,245,814 B1
(45) Date of Patent: Jun. 12, 2001

(54) DIPHENYLETHYLENE COMPOUNDS

(75) Inventors: Bishwajit Nag, Fremont; Satyanarayana Medicherla, Sunnyvale; Debendranath Dey, Union City, all of CA (US)

(73) Assignee: Calyx Therapeutics, Inc., Hayward, CA (US)

( * ) Notice: Subject to any disclaimer, the term of this patent is extended or adjusted under 35 U.S.C. 154(b) by 0 days.

(21) Appl. No.: 09/074,925

(22) Filed: May 8, 1998

(51) Int. Cl.$^7$ ..................................................... A61K 31/19
(52) U.S. Cl. .............................................................. 514/570
(58) Field of Search ............................................ 514/570

(56) References Cited

U.S. PATENT DOCUMENTS

| | | |
|---|---|---|
| 3,609,183 | 9/1971 | DeWald et al. . |
| 3,683,009 | 8/1972 | Middleton . |
| 4,217,366 | 8/1980 | Kikumoto et al. . |
| 4,271,186 | 6/1981 | Forster et al. . |
| 4,284,637 | 8/1981 | Kikumoto et al. . |
| 4,310,534 | 1/1982 | Kikumoto et al. . |
| 4,312,855 | 1/1982 | Grand . |
| 4,326,055 | 4/1982 | Loeliger . |
| 4,716,905 | 1/1988 | Schmued . |
| 4,866,086 | 9/1989 | Boyle et al. . |
| 4,929,635 | 5/1990 | Coquelet et al. . |
| 4,940,707 | 7/1990 | Klaus et al. . |
| 5,087,637 | 2/1992 | Janssen et al. . |
| 5,162,337 | 11/1992 | Elbrecht et al. . |
| 5,171,753 | 12/1992 | Munson, Jr. et al. . |
| 5,189,056 | 2/1993 | Orlando et al. . |
| 5,246,936 | 9/1993 | Treacy et al. . |
| 5,250,562 | 10/1993 | Klaus et al. . |
| 5,314,693 | 5/1994 | Suga . |
| 5,378,705 | 1/1995 | Klaus et al. . |
| 5,409,953 | 4/1995 | Pettit et al. . |
| 5,430,062 | 7/1995 | Cushman et al. . |
| 5,494,932 | 2/1996 | Cardin et al. . |
| 5,521,160 | 5/1996 | Chucholowski et al. . |
| 5,525,632 | 6/1996 | Obsumi et al. . |
| 5,532,129 | 7/1996 | Heller . |
| 5,559,151 | 9/1996 | Adorante et al. . |
| 5,565,191 | 10/1996 | Raspanti . |
| 5,565,322 | 10/1996 | Heller . |
| 5,569,786 | 10/1996 | Pettit et al. . |
| 5,583,128 | 12/1996 | Bhatnagar . |
| 5,589,506 | 12/1996 | Hashimoto et al. . |
| 5,672,625 | 9/1997 | Cardin et al. . |
| 5,674,906 | 10/1997 | Hatanaka et al. . |
| 5,705,530 | 1/1998 | Adorante et al. . |
| 5,716,928 | 2/1998 | Benet et al. . |
| 5,731,353 | 3/1998 | Ohsumi et al. . |
| 5,733,909 | 3/1998 | Black et al. . |
| 5,767,268 | 6/1998 | Chucholowski et al. . |
| 5,770,620 | 6/1998 | Mjalli et al. . |
| 5,827,898 | 10/1998 | Khandwala et al. . |

OTHER PUBLICATIONS

Pettit et al., "Isolation, Structure, Synthesis, and Antimitotic Properties of Combretastatins B–3 and B–4 from Combretum Caffrum," *Journal of Natural Products*, vol. 51, No. 3, pp. 517–527, 5/1988.

Green, R.H. Syntheses of Differanisole A. Tetrahedron Lett., 1997, vol. 38, No. 26, pp. 4697–4700.

Reddy, K.L. et al., "From Styrenes to Enantiopure alpha–Arylglycines in Two Steps", J.Am.Chem.Soc. 1998, vol. 120, No. 6, pp. 1207–1217, 1209 and 1211.

*Primary Examiner*—Samuel Barts
(74) *Attorney, Agent, or Firm*—Pillsbury Winthrop LLP

(57) ABSTRACT

Novel diphenylethylene and styrenes are provided which are administered orally to decrease blood glucose levels in rats. The glucose tolerance in insulin resistant rats is also shown, as well as lowering of triglyceride levels in serum insulin resistant, hyperinsulinemic and hypertriglycedemic rats. The compounds are orally effective anti-diabetic agents that potentially may reduce abnormality of glucose and lipid metabolism in diabetes.

2 Claims, 4 Drawing Sheets

Effect of drug on blood glucose levels in STZ induced diabetic rats
VEHICLE: (n=6) PBS oral
DRUG: (n=6) drug at a dose of 20 mg/kg/BW, oral
BLOOD GLUCOSE (% of 0-time)

| TIME (mts) | VEHICLE | |
|---|---|---|
| 0 | 100 | 100 |
| 30 | 355 | 326 |
| 60 | 385 | 342 |
| 120 | 371 | 240 |

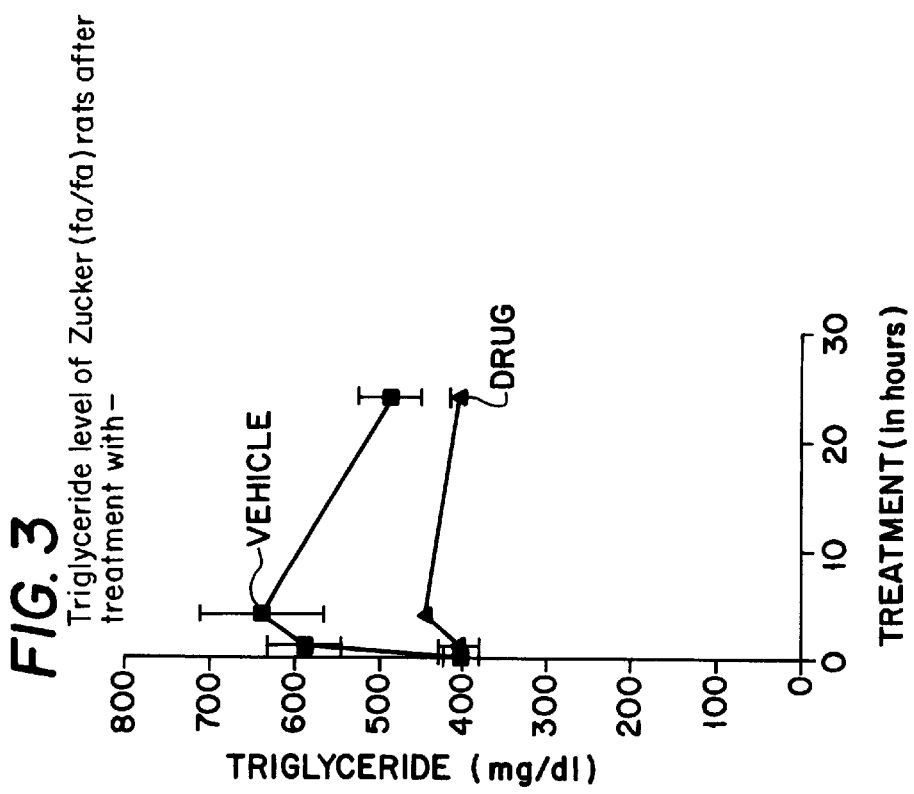
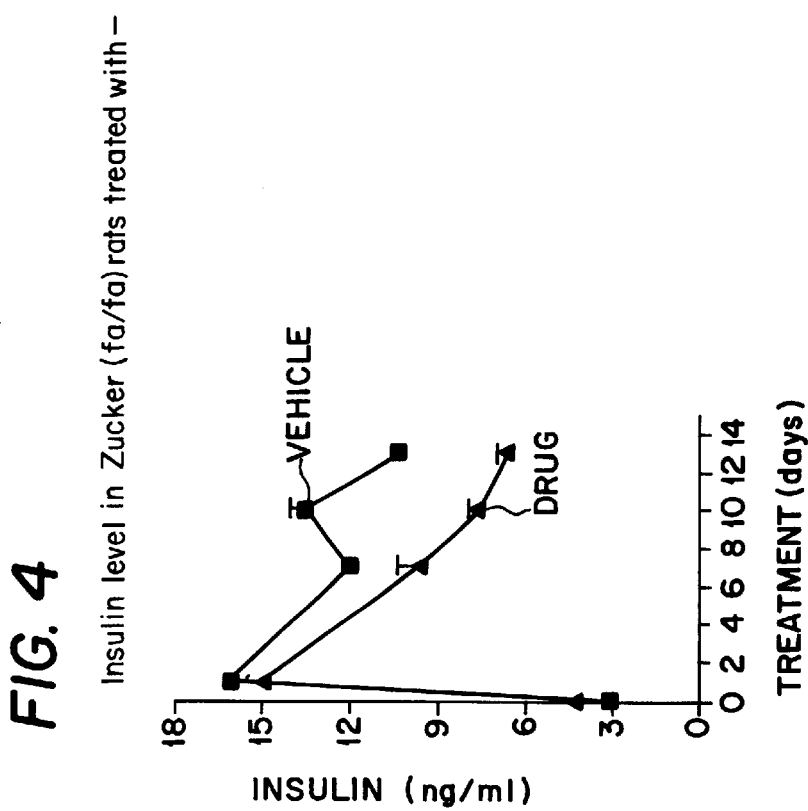

STUDY-1 (500 ug/mouse)

| Day | Animals alive |
|---|---|
| 0 | 3 |
| 1 | 3 |
| 2 | 3 |
| 3 | 3 |
| 4 | 3 |

STUDY-2 (5mg/mouse)

| Day | Animals alive |
|---|---|
| 0 | 3 |
| 1 | 3 |
| 2 | 3 |
| 3 | 3 |
| 4 | 3 |

STUDY-3 (10 mg/mouse)

| Day | Animals alive |
|---|---|
| 0 | 3 |
| 1 | 3 |
| 2 | 3 |
| 3 | 3 |
| 4 | 3 |

DIPHENYLETHYLENE COMPOUNDS

FIELD OF THE INVENTION

The field of the invention is novel diphenylethylene compounds and their use for treatment of diabetes.

BACKGROUND OF THE INVENTION

Extracts of the leaves, flowers, and gum of the tree *Pterocarpus marsupium* Roxb. (Leguminosae), also known as the Indian Kino Tree, have been used traditionally for the treatment of diarrhea, toothaches, fever and urinary and skin infections. Extracts of the bark have been long regarded as useful for the therapy of diabetes. Hypoglycemic activity of a naturally occurring pterostilbene, trans-1-(3,5-dimethoxyphenyl)-2-(4-hydroxyphenyl)-ethylene, isolated from the heartwood of pterocarpus marsupium as been reported by Manickam et al., *J. Nat. Prod.*, 1997, 60:609–610. However, this pterostilbene is water insoluble and has not been shown to be efficacious in the treatment of diabetes, particularly in instances where insulin is present but inactive. The cause of diabetes is yet unknown, although both genetics and environment appear to be factors. Insulin dependent (Type I) and non-insulin dependent (Type II) are the types of diabetes. Type I is an autonomic immune disease in which the responsible autoantigen is still unknown. Patients of Type I need to take insulin intravenously to survive. However, Type II diabetes, the more common form of the disease, is a metabolic disorder resulting from the body's inability to make a sufficient amount of insulin or to properly use the insulin that is produced within the body. Insulin secretion and insulin resistance are considered the major defects, however, the precise genetic factors involved in the mechanism remain unknown.

Patients with diabetes usually have one or more of the following defects: less production of insulin by the pancreas; over secretion of glucose by the liver; impairment of glucose uptake by the skeletal muscle; defects in glucose transporters; desensitation of insulin receptors; and defects in the metabolic breakdown of polysaccharides. Other than the intravenous application of insulin, there are four classes of oral hypoglycemic agents in use.

| Class | Approved Drugs | Mechanisms of Action | Limitations |
|---|---|---|---|
| sulfur urea | 4 (1st generation) and 2 (2nd generation) | acts on pancreas to release more insulin | dev. of resistance |
| biguanides | metformin | reduces glucose secretion by liver; improves insulin sensitivity | liver problems, lactic acidosis |
| alpha-glucosidase inhibitor | acarbose | interferes with digestive process; reduces glucose absorption | only useful at post-pradiandio level |
| thiazolidine-dione | troglipzone | reduces insulin resistancy | "add-on" with insulin; not useful for people with heart and liver disease |

As is apparent from the above table, each of the current agents available for use and treatment of diabetes has certain disadvantages. Accordingly, there is a continuing interest in the identification and development of new agents, particularly, water soluble agents which can be orally administered, for the use of treatment of diabetes.

Besides the pterostilbene discussed above, (-)-epicatechin, has also been isolated from pterocarpus marsupium by Sheehan et al., *J. Nat. Prod.*, 1983, 46:232, and has been reported as having a hypoglycemic effect. See also Chakravarthy et al., *Life Sciences*, 1981, 29:2043–2047. Other phenolic type compounds have been isolated from pterocarpus marsupium by Maurya et al., *J. Nat. Prod.*, 1984, 47:179–181; Jahromi et al., *J. Nat. Prod.*, 1993, 56:989–994; and Maurya et al., *Heterocycles*, 1982, 19:2103–2107.

SUMMARY OF THE INVENTION

A class of novel diphenylethylenes is provided having the following formula I.

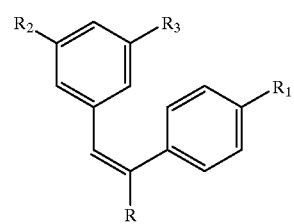

(I)

wherein R is hydrogen or —$CO_2Z$, Z is hydrogen or a cation;

and $R_1$, $R_2$ and $R_3$ are each independently H, —OH or —$OR_4$, wherein $R_4$ is linear or branched alkyl of 1–12 carbon atoms; with the proviso that when R is hydrogen and $R_2$=$R_3$=—OMe, then $R_1$ is not —OH.

A novel class of styrenes is also provided of the formula II

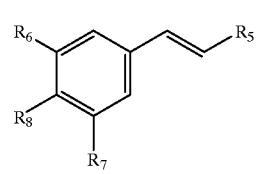

(II)

wherein $R_5$ is hydrogen or methyl; $R_6$ and $R_7$ are independently hydrogen or OMe; $R_8$ is hydrogen or hydroxy.

Pharmaceutical compositions of compounds of the formula I or II are provided for treatment of diabetes comprising of therapeutically effective amount of the compound in a physiologically acceptable carrier.

A method of treating diabetes is also provided comprising step of orally administering to a subject suffering from a diabetic condition a therapeutically effective amount of a compound of formula I or II.

BRIEF DESCRIPTION OF THE DRAWING

FIG. 3 shows the effect of the compound in Example 1 on plasma triglyceride levels in Zucker rats.

FIG. 4 shows the effect of the compound in Example 1 on glucose tolerance in Zucker rats.

DESCRIPTION OF THE PREFERRED EMBODIMENTS

Figure 1:
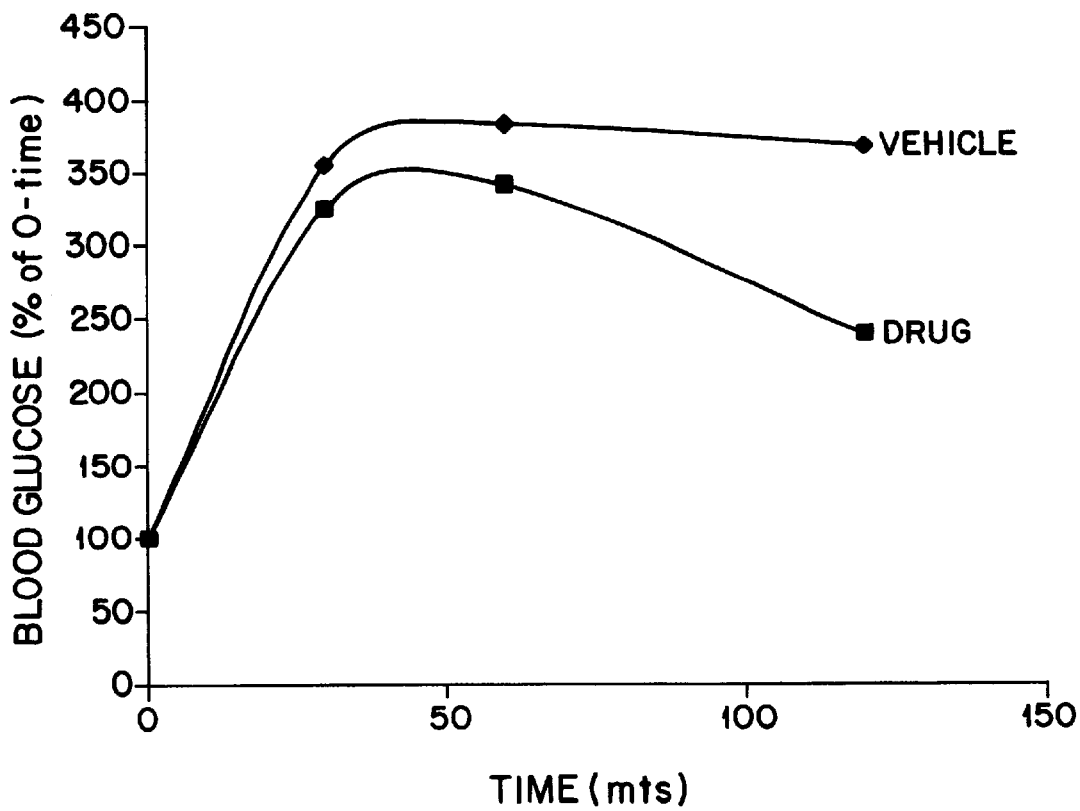
FIG. 1 shows the effect of administration of the compound in Example 1 on blood glucose level in STZ induced diabetic rats.

Diphenylethylene of the formula I and styrenes of formula II are provided by synthetic methods generally known in the art. Particularly, preferred are compounds of formula I in which $R_2$ and $R_3$ are methoxy. A particularly preferred species is a compound in which $R_2$ and $R_3$ are methoxy and R is $CO_2Z$, and $R_1$ is OH. The cations for Z are typically sodium, lithium, potassium, or any other physiologically acceptable cation which may be introduced orally to a subject.

Particularly preferred styrenes of the formula II are those in which $R_6$ and $R_7$ are methoxy and $R_8$ is hydrogen. Another preferred class of the formula II includes compounds wherein $R_6$ and $R_7$ are hydrogen and $R_8$ is hydroxy.

The compounds of the formula I and II are made by methods known in the art. In general, for the compounds of formula I, appropriate benzaldehyde and phenylacetic acid starting materials are condensed, then decarboxylated, if required.

SCHEME 1

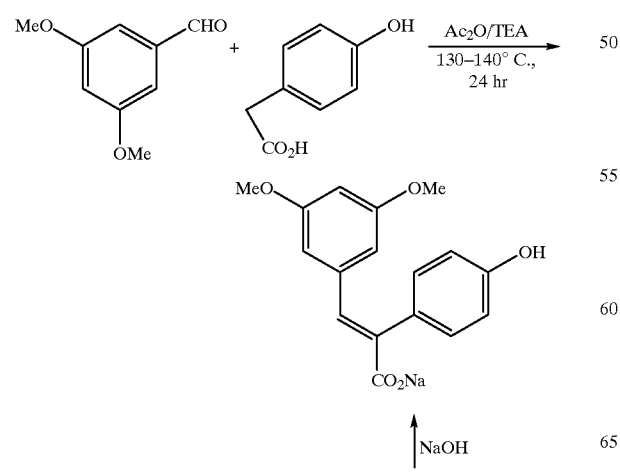

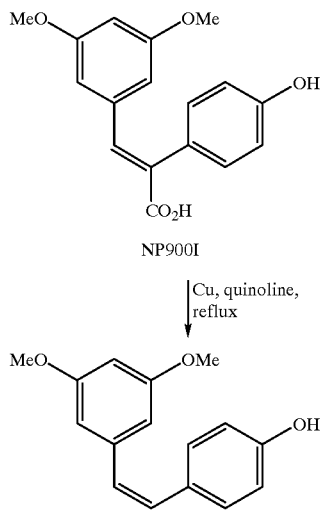

Compounds of the formula II are prepared generally from a benzaldehyde starting material and alkylidenetriphenylphosphorane by the Wittig reaction.

SCHEME II

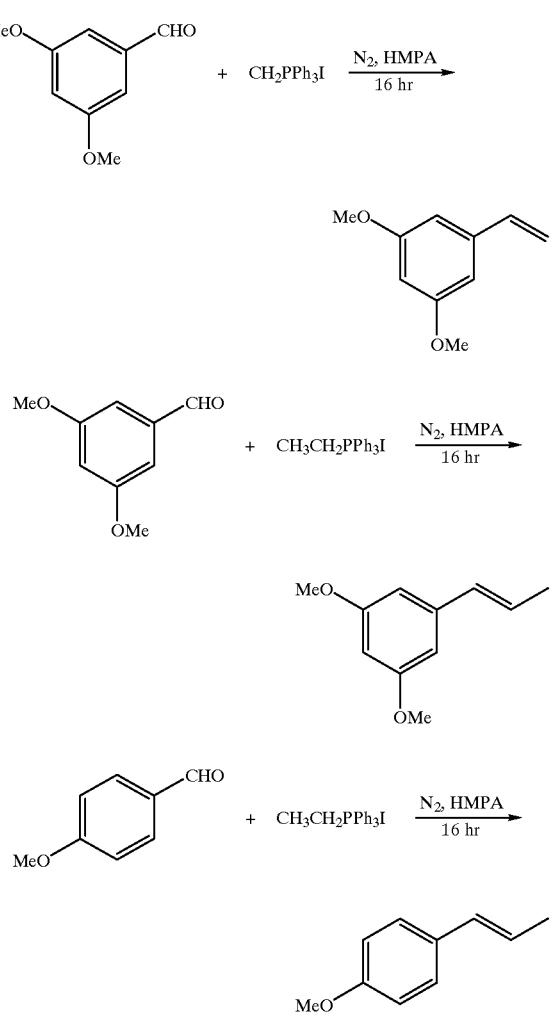

Exemplary compounds of the formula I and II are as follows:

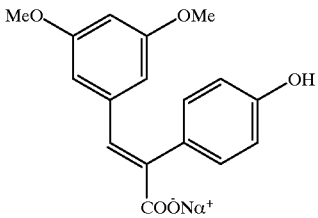

1

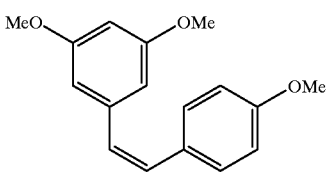

2

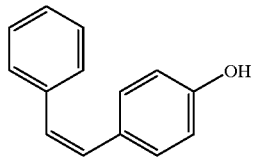

3

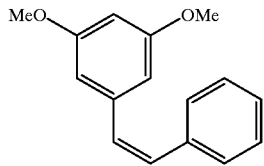

4

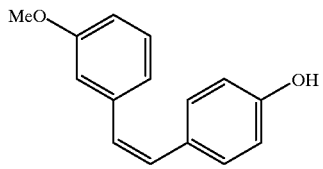

5

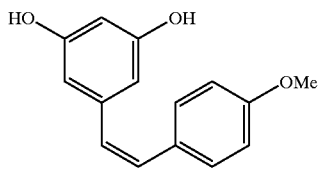

6

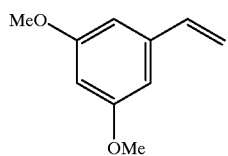

7

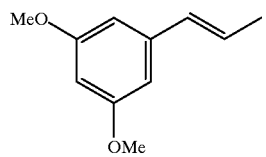

8

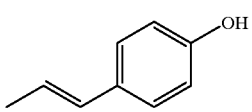

9

The compounds according to the present invention may be combined with a physiologically acceptable vehicle in pharmaceutical composition. The particularly preferred form of composition is an orally administrated capsule or solution in which the compound is delivered in water, saline, a phosphate buffer, or lyophilized powder in a form of tablets or capsules which also includes various fillers and binders. The effective dosages of the compound in a composition will be selected by those of ordinary skill in the art and may empirically be determined.

The compounds of the present invention are useful for the treatment of diseases such as diabetes characterized by the presence of elevated blood glucose levels, that is, hyperglycemic disorders such as diabetes melitus, including both Type I and II diabetes as well as other hyperglycemic related disorders such as obesity, increased cholesterol, kidney related disorders, and the like.

By "treatment", it is meant that the compound is administered at least to reduce the blood glucose level in the patient suffering from the hyperglycemic disorder. The compound is administered in an amount sufficient to reduce blood glucose level to an acceptable range, wherein an acceptable range means ±10%, usually ±8% and usually ±5% of the normal average blood glucose level for the subject. A variety of subjects may be treated with the compounds to reduce blood glucose levels, such as livestock, valuable or rare animals, pets, as well as humans. The compounds may be administered to the subject suffering from the hyperglycemic disorder using a convenient administration technique, including intravenous, intradermal, intramuscular subcutaneous oral and the like. However, the oral route of administration is particularly preferred. The dosage delivered to the host will necessarily depend upon the route by which the compound is delivered, but generally ranges from 5 to 500 mg/70 kg human body weight or typically from about 50 to 200 mg/70 kg human body weight. Of particular interest are methods of treating human hyperglycemic disorder such as diabetes, including both Type I and II, where the compound is administered to the human suffering from the hyperglycemic disorder to at least reduce the blood glucose level of the subject to about the normal blood glucose range for a human.

The following examples are offered by way of illustration and not intended to limit the invention in any way.

EXAMPLE 1

Preparation of Sodium 2-(4-hydroxyphenyl)-3-(3,5-dimethoxyphenyl)-propenoate

To a mixture of 3,5-dimethoxybenzaldehyde (30 mM) and P-hydroxyphenyl acetic acid (30 mM) was added 5 mL acetic anhydride and 2.5 mL of triethylamine (TEA). After being stirred at 130–140° C. for 24 hr., the mixture was cooled to room temperature and quenched with 25 mL concentrated HCl and extracted with $CH_2Cl_2$. The organic extract was further extracted with 1N NaOH, then the NaOH extract was washed with water, the aqueous layer was acidified with concentrated HCl and washed with water to obtain the crude product. Crude product was recrystallized from ethanol/water to yield the acid I.

To decarboxylate I, 1 g under $N_2$, 3 g of Cu powder and 30 mL of quinoline were refluxed, stirring for 4 hrs. The reaction mixture was filtered, diluted with water and extracted with $CH_2Cl_2$. The organic layer was dried and concentrated, and the decarboxylated product was purified by flash chromatography.

To convert the acid I to the title compound, to 1 g of I NaOH solution was added under room temperature. The mixture was shaken and freeze dried to give acid salt title product, 1.

EXAMPLE 2

General Procedure for Preparation of Styrene Derivatives

General Procedure: To a stirred solution of Wittig salt (1 mM) in dry THF at −78° C. was added potassium (bistrimethylsilyl)amide (1 mM). After being stirred under $N_2$ for 2 hours at −78° C., HMPA (2 mM) and aldehyde (1 mM) in THF was added and stirred at room temperature for 16 hours. The reaction was quenched with water and extract with diethyl ether. Product was purified by flash chromatography.

EXAMPLE 3

Referring to FIG. 1, the streptozotocin (STZ)-induced diabetic rats were produced by injecting STZ (40 mg/kg/BW) intravenously. The blood glucose levels were measured 72 hrs. after the injection. Experiments were conducted with rats showing fasting blood glucose levels more than 200 mg/dl. The compound in example 1 was administered at a dose of 20 mg/kg/BW orally to test rats. Simultaneously, a control group received vehicle PBS (phosphate buffered saline). Soon after administration, glucose tolerance tests were conducted by administering glucose (2 g/kg/BW) and blood glucose levels were monitored at different time points. The results are shown in FIG. 1. Between 30 and 60 minutes after administration, the blood glucose levels in the rats receiving the test compound began to diminish.

EXAMPLE 4

Figure 2:
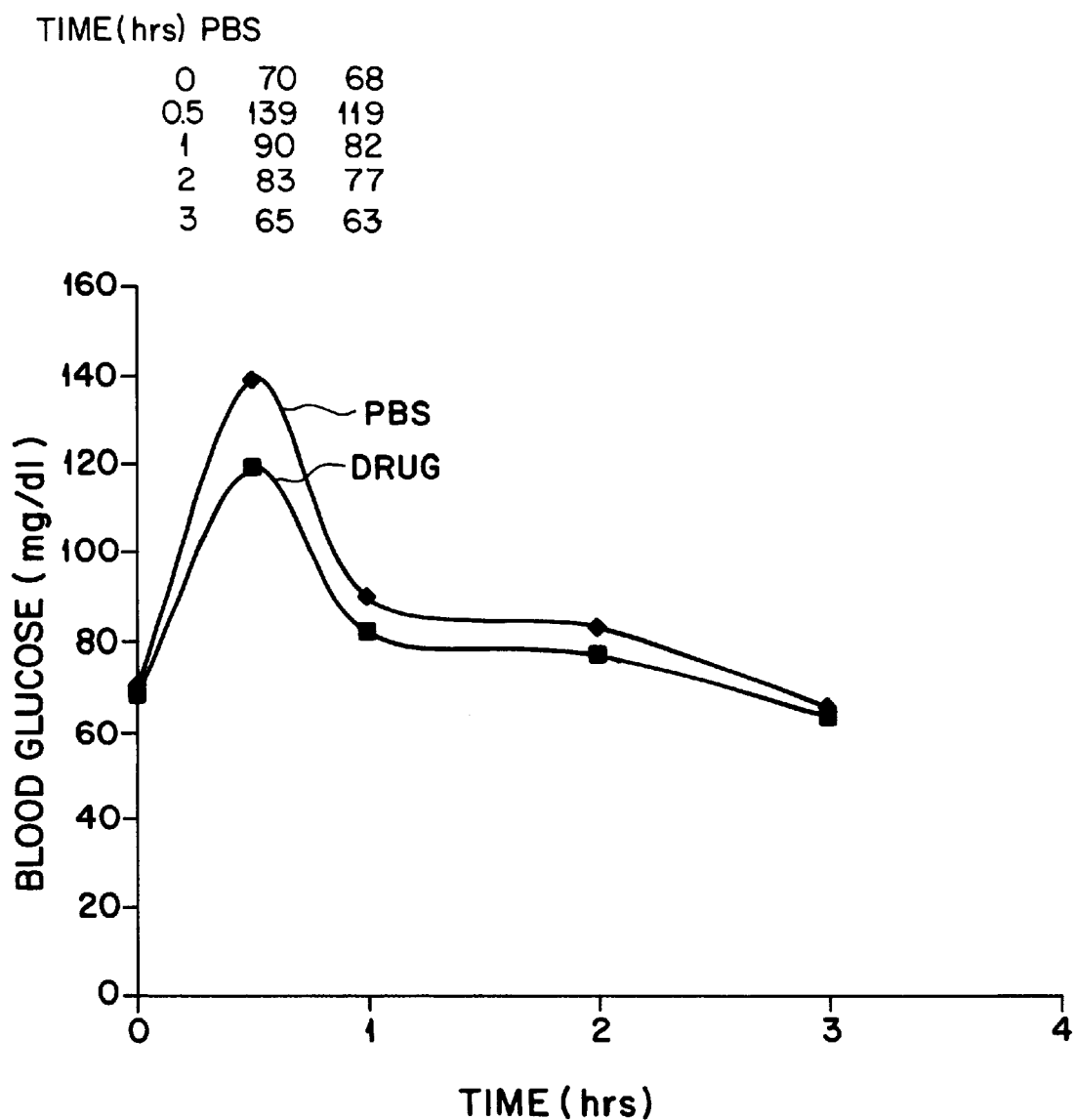
FIG. 2 shows the effect of the compound in Example 1 on glucose tolerance in hyperinsulinemic and insulin resistant Zucker rats.

Referring to FIG. 2, glucose tolerance was measured in Zucker (fa/fa) rats. Hyperinsulinemic and insulin resistant Zucker rats were randomized into two groups designated as a test group and a control group to check the effect of compound in Example 1 on glucose tolerance and insulin levels. Six of the test group rats were given dosages of the compound of Example 1 (20 mg/kg/BW/oral) once per day for period of three days. The control group was gavaged with an equal volume of PBS. An oral glucose (2 g/kg/BW) tolerance test was conducted on overnight-fasted rats soon after administration of test materials on day-3. Referring to FIG. 2, it shows that the compound of Example 1 improves glucose tolerance in insulin resistant obese Zucker rats.

EXAMPLE 5

Referring to FIG. 3, twelve insulin resistant hyperinsulinemic obese Zucker (fa/fa) rats were randomized into two groups designated as a test group and a control group. Six of the test group rats received the compound of Example 1 (20 mg/kg/BW) at zero hour. The control group received an equal volume PBS. Plasma triglyceride levels were monitored for a period of 24 hours on fed state. The results are shown in FIG. 3. The compound from Example 1 lowers plasma triglyceride levels in obese insulin resistant hyperinsulinemic and triglyceridemic Zucker rats.

EXAMPLE 6

Referring to FIG. 4, twelve obese hyperinsulinemic and insulin resistant Zucker (fa/fa) rats were randomized into groups designated as the test group and control group. Six of the test group were kept on the compound of Example 1 (20 mg/kg/BW/oral) once per day for a period of thirteen days. The control group was gavaged with an equal volume of PBS. Basal plasma insulin levels were monitored intermittently every three or four days during the course of the thirteen day study. The results in FIG. 4 show that the compound has an effect on lowering plasma insulin levels in this animal model.

EXAMPLE 7

Figure 5A:
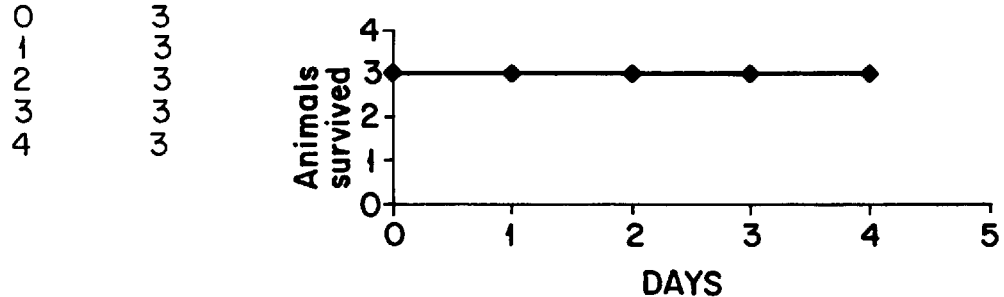
FIGS. 5A, 5B and 5C show, respectively, results of a lethal effect study on Swiss Webster mice by administration of dosages of 16.7, 167, and 333 mg/kg/BW on day zero.
Figure 5B:
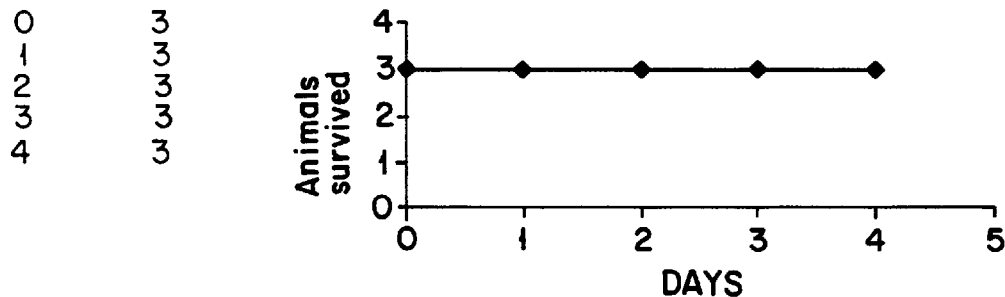
Figure 5C:
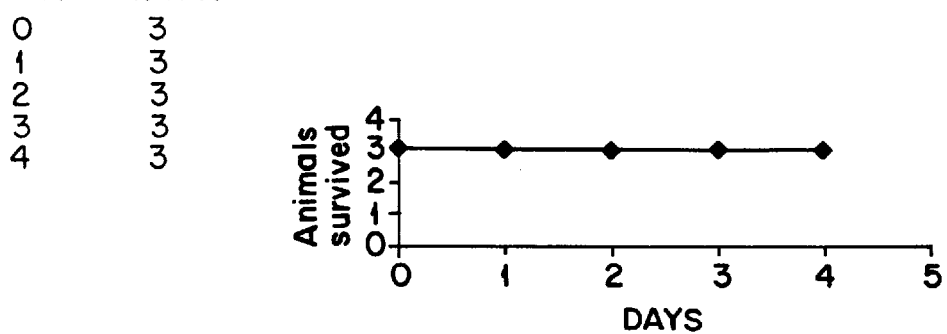

Nine healthy male Swiss Webster mice were divided into three study groups of three. The first study group (FIG. 5A) received the compound of Example 1 at a dose of 16.7 mg/kg/BW, the second study group (FIG. 5B) received a dose of 167 mg/kg/BW, and the third study group (FIG. 5SC) received a dose of 333 mg/kg/BW on day zero of the study. The mice were kept on regular food and water during the entire study period. During the study, the mice were under close observation and their behavior, gross physiology and mortality/survival were monitored. FIGS. 5A, 5B and 5C show that the survival rate in these mice in the course of the study period was 100%.

What is claimed is:

1. A method of treating diabetes comprising a step of administering to a subject suffering from a diabetic condition a therapeutically effective amount of a compound

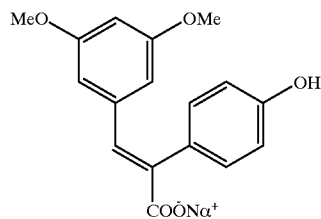

in a physiologically acceptable carrier.

2. A method according to claim 1, wherein said compound is orally administered to said subject.

* * * * *